United States Patent
Ogawa (10) Patent No.: US 10,238,817 B2
(45) Date of Patent: Mar. 26, 2019

(54) PREFILLED SYRINGE

(71) Applicant: Terumo Kabushiki Kaisha, Tokyo (JP)

(72) Inventor: Junichi Ogawa, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 658 days.

(21) Appl. No.: 14/790,924

(22) Filed: Jul. 2, 2015

(65) Prior Publication Data

US 2016/0001017 A1 Jan. 7, 2016

(30) Foreign Application Priority Data

Jul. 3, 2014 (JP) .................................. 2014-137938

(51) Int. Cl.
| | |
|---|---|
| *A61M 5/50* | (2006.01) |
| *A61M 5/315* | (2006.01) |
| *A61M 5/31* | (2006.01) |
| *A61M 5/46* | (2006.01) |

(52) U.S. Cl.
CPC ........ *A61M 5/5086* (2013.01); *A61M 5/3129* (2013.01); *A61M 5/3135* (2013.01); *A61M 5/3157* (2013.01); *A61M 5/31501* (2013.01); *A61M 5/46* (2013.01); *A61M 2005/312* (2013.01); *A61M 2005/3125* (2013.01); *A61M 2205/583* (2013.01); *A61M 2205/584* (2013.01)

(58) Field of Classification Search
CPC .............. A61M 5/3135; A61M 5/5086; A61M 5/31501; A61M 5/3157; A61M 2205/583; A61M 2205/584
See application file for complete search history.

(56) References Cited

U.S. PATENT DOCUMENTS

2011/0092915 A1* 4/2011 Olson ................. A61M 5/3202
604/198
2013/0079729 A1 3/2013 Yokota et al.

FOREIGN PATENT DOCUMENTS

| EP | 2 698 179 A1 | 2/2014 |
| WO | WO-2011/047298 A2 | 4/2011 |
| WO | WO-2011/122221 A1 | 10/2011 |
| WO | WO-2014/122782 A1 | 8/2014 |

OTHER PUBLICATIONS

Extended European Search Report issued in corresponding application No. 15174071.9 dated Oct. 22, 2015.

* cited by examiner

*Primary Examiner* — Nathan R Price
*Assistant Examiner* — Justin L Zamory
(74) *Attorney, Agent, or Firm* — Foley & Lardner LLP (57) ABSTRACT

A prefilled syringe includes: a syringe barrel including a syringe barrel body and an outer barrel; a cap; a gasket; and a plunger which allows the gasket to slide by pressing a press portion located on the base end of a shaft to discharge a drug solution inside the syringe barrel body. The outer barrel has a window and a mask which hides the inside of the outer barrel on a wall thereof. A part of the shaft has a mark which has a color different from the color of other parts of the plunger. The mark is covered with the mask and is not visually recognizable through the window before discharge of the drug solution. The outer peripheral surface of the mark is visually recognizable through the window along with movement of the plunger when the discharge of the drug solution is completed.

15 Claims, 9 Drawing Sheets

PREFILLED SYRINGE

CROSS-REFERENCE TO RELATED APPLICATIONS

This application claims priority to Japanese Patent Application No. 2014-137938, filed on Jul. 3, 2014, which is hereby incorporated by reference in its entirety.

BACKGROUND

Technical Field

The present invention relates to a prefilled syringe which, after previous storage and discharge of a drug solution in a syringe barrel, clearly indicates that the prefilled syringe has already been used.

Related Art

In order to prevent contamination of an injection drug solution caused by bacteria, and achieve simplified injection drug solution preparation, a drug solution is administered to a subject, for example, a patient using a prefilled syringe which previously stores a drug solution in a syringe barrel. In the prefilled syringe, a plunger which has a gasket in a tip region and a press portion in a base end region is inserted into the syringe barrel that stores the drug solution. Pressing the press portion allows the gasket to slide inside the syringe barrel, so that the drug solution is injected into the subject through an injection needle attached to a tip of the syringe barrel.

The amount of a drug solution of a bio-pharmaceutical such as an influenza vaccine to be administered to a subject is small, specifically, 1 mL or less. Further, when a drug solution is administered into the skin, the administration amount is extremely small, specifically, 0.5 mL or less. A prefilled syringe filled with such a small amount of drug solution has a syringe barrel having a small inner diameter corresponding to the drug solution amount, and the outer diameter of the syringe barrel thus becomes also small. Therefore, it is difficult for an operator, for example, a doctor to tightly hold the prefilled syringe during administration. As a prefilled syringe taking into consideration the above problem, WO 2011/122221 A1 discloses a drug administration device provided with a syringe barrel body which has a fluid chamber capable of accommodating a drug therein and a discharge section formed at the tip thereof, a plunger which is connected to a gasket slidably movable within the fluid chamber and has a shaft part of which is exposed outside from a tubular body, an outer barrel which is disposed outside the syringe barrel body and kept away from the tubular body, and a connection section which connects the syringe barrel body and the outer barrel. This drug administration device makes it possible to support and stabilize the outer barrel together with the syringe barrel body by tightly gripping the outer barrel with the entire palm, and to smoothly administer a drug solution.

SUMMARY

However, in a prefilled syringe filled with a small amount of drug solution, the stroke, which is movement distance of a plunger required for administration of the drug solution, is short. Thus, even when a gasket has reached the tip of the inner wall of a syringe barrel body, a change in the appearance of the position of the base end of the plunger—that is, a difference in the projection length of the plunger from an outer barrel before and after the administration of the drug solution—is small. Therefore, it is difficult to distinguish whether the prefilled syringe has already been used.

Consequently, there is a need for a prefilled syringe as a medical device having high safety that is capable of distinguishing whether the prefilled syringe has already been used at a glance even when the movement distance of a plunger is short due to a small amount of drug solution filled therein. One object of certain embodiments of the present invention is to address the above problem by, for example, providing a prefilled syringe which is provided with an outer barrel having an inner diameter larger than the inner diameter of a syringe barrel body and capable of easily and surely distinguishing between an unused condition and a used condition of the prefilled syringe by visual observation even when the movement distance of a plunger is short.

A prefilled syringe of the present invention which has been made to achieve the above object is provided with: a syringe barrel including a syringe barrel body and an outer barrel, the syringe barrel body having a drug solution discharge portion located on a tip and an insertion port open on a base end, at least a part of the outer barrel extending in a tubular shape from a circumference of the insertion port toward a base end side, the outer barrel having an opening located on a base end and having an inner diameter larger than the inner diameter of the syringe barrel body from the circumference of the insertion port through the opening; a cap configured to seal the drug solution discharge portion; a gasket inserted into the syringe barrel body; a plunger having a shaft inserted into the syringe barrel through the opening and a press portion disposed on a base end of the shaft, the plunger being configured to move toward a tip by a pressing operation to the press portion to allow the gasket to slide toward the drug solution discharge portion; and a drug solution stored between the drug solution discharge portion and the gasket inside the syringe barrel body, the drug solution being configured to be discharged from the drug solution discharge portion by the slide of the gasket, wherein the outer barrel has a window formed on a wall of the outer barrel located between the insertion port and the opening and a mask configured to hide the inside of the outer barrel, a mark is disposed on one part of the shaft located between the insertion port and the opening, the mark having an outer diameter larger than the inner diameter of the syringe barrel body and having a color different from a color of the other part of the plunger at least on an outer peripheral surface of the mark, and the outer peripheral surface of the mark is covered with the mask and the mark cannot be visually recognized through the window from a direction inclined by 70° or more with respect to a central axis of the outer barrel before discharge of the drug solution, and the outer peripheral surface of the mark which has moved along with movement of the plunger toward the tip can be visually recognized through the window when the discharge of the drug solution is completed.

In the prefilled syringe, the mark may be formed by fitting a mark member having a color different from the color of the other part of the plunger at least on an outer peripheral surface of the mark member onto the one part of the shaft.

Preferably, in the prefilled syringe, the outer barrel includes a substantially transparent outer barrel body and a label, the label being configured to cover the entire circumference of an outer peripheral surface of the outer barrel body and having a transparent portion or an exposure portion configured to expose the outer peripheral surface of the outer barrel body and two opaque portions located on a tip side and a base end side of the transparent portion, the window includes a wall of the outer barrel body and the transparent portion or the exposure portion of the label, and the mask includes the opaque portions.

In the prefilled syringe, the window may be continuously or intermittently formed on the entire circumference around a central axis of the outer barrel body.

Preferably, in the prefilled syringe, the width of the transparent portion or the exposure portion in a central axis direction of the outer barrel is within the range of 0.5 to 1 mm.

Preferably, in the prefilled syringe, the mark member is formed in a ring-like shape a part of which has a cut-away part and fitted onto the shaft from a direction substantially perpendicular to a central axis of the shaft using the cut-away part, the shaft has a tip side flange located on the tip side with respect to the mark member, the tip side flange extending in a direction substantially perpendicular to the central axis of the shaft, and the tip side flange is located on the base end side with respect to the window before discharge of the drug solution.

Preferably, in the prefilled syringe, the shaft has a base end side flange located between the mark and the opening, the base end side flange extending in a direction substantially perpendicular to the central axis of the shaft.

In the prefilled syringe, the outer barrel may have a substantially transparent outer barrel body and a label, the label being configured to cover the entire circumference of an outer peripheral surface of the outer barrel body and having an opaque portion serving as the mask, and the window may include a wall of the outer barrel body, the wall not being covered with the label.

Preferably, in the prefilled syringe, a maximum movement distance of the plunger between start and completion of discharge of the drug solution is 15 mm.

Preferably, in the prefilled syringe, the inner diameter of the syringe barrel body is 7 mm or less.

The prefilled syringe of the present invention stores a drug solution inside the syringe barrel body. When the discharge of the drug solution is completed, the mark which indicates whether the drug solution has been discharged or not is exposed through the window so as to be visually recognizable. In the prefilled syringe, the mark is exposed at a conspicuous position between the middle and the base end of the outer barrel. Further, in the prefilled syringe, the coloring and the shape of the mark or the shape of the window makes the exposure of the mark conspicuous. Thus, it is possible to much surely distinguish between a used condition and an unused condition compared to a conventional prefilled syringe in which a change in the projection length of a plunger before and after the discharge of a drug solution is small and a used condition and an unused condition are thus likely to be misrecognized merely by visual observation.

DETAILED DESCRIPTION

Hereinbelow, embodiments of the present invention will be described in detail. However, the scope of the present invention is not limited to these embodiments.

Figure 1:
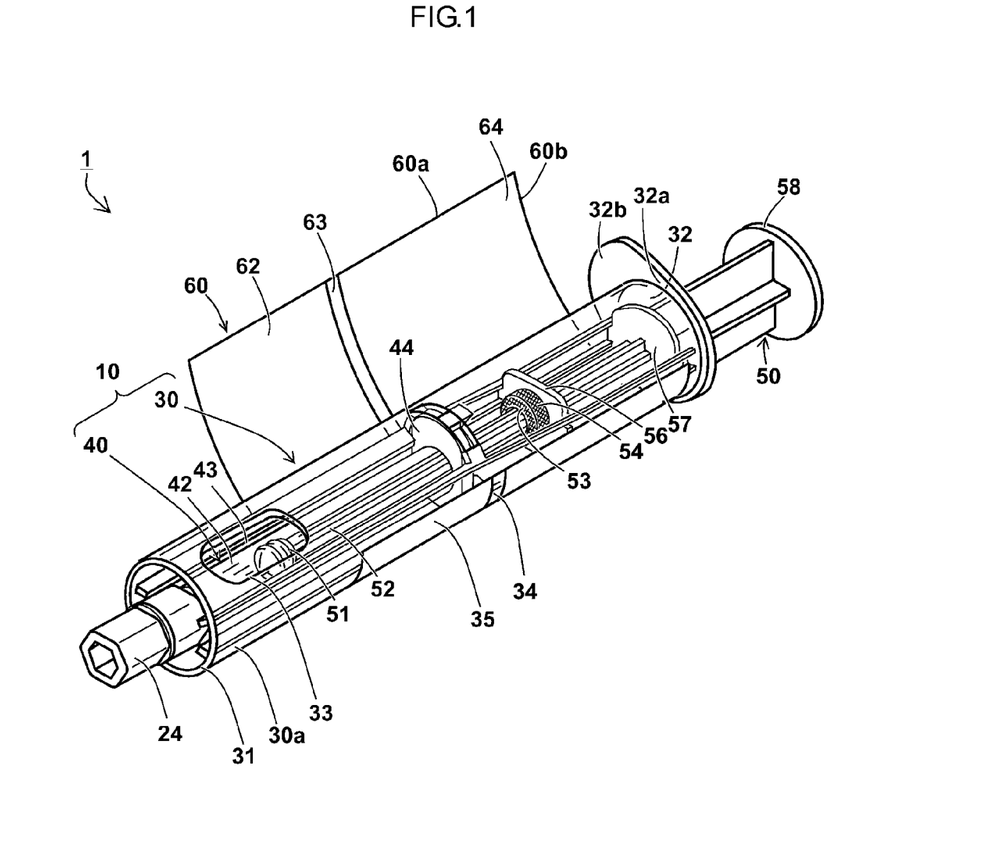
FIG. 1 is a partially exploded perspective view illustrating an embodiment of a prefilled syringe of the present invention.

FIG. 1 is a partially exploded perspective view illustrating an embodiment of a prefilled syringe 1 of the present invention. The prefilled syringe 1 is provided with a syringe barrel 10 which includes an outer barrel 30, the outer barrel 30 having a window 34 and a mask 35 formed by a label 60 covering the outer peripheral surface of an outer barrel body 30a, and a syringe barrel body 40 inserted into and fixed to the outer barrel 30, a gasket 51 which is slidably inserted into the syringe barrel body 40, a plunger 50 which allows the gasket 51 to slide, and a cap 24 which seals the tip of the syringe barrel body 40, the cap 24 being replaceable with an injection hub 20 (refer to FIGS. 2A to 2C). FIG. 1 illustrates a state in which a part of the label 60 is peeled off the outer peripheral surface of the outer barrel body 30a.

The syringe barrel body 40 is molded of a transparent resin so that the inside thereof can be visually recognized. The syringe barrel body 40 has, on the tip thereof, a drug solution discharge portion 41 and a luer lock adapter 45 which surrounds a part of the side face of the drug solution discharge portion 41 (refer to FIG. 2A). The syringe barrel body 40 further has, on the base end thereof, an insertion port 46 (refer to FIG. 3) and a syringe barrel flange 44 which projects outward in the radial direction from the peripheral edge of the insertion port 46. The syringe barrel body 40 further has a body 43 which is provided with an inner space and located between the drug solution discharge portion 41 and the insertion port 46. The outer edge of the syringe barrel flange 44 viewed from the base end side has a shape having a long axis and a short axis. The syringe barrel flange 44 has a pair of long axis direction side faces 44a located on opposite sides in the long axis direction and a pair of short axis direction side faces 44b located on opposite sides in the short axis direction (refer to FIG. 3). The outer edge of each of the long axis direction side faces 44a viewed from the base end side has a circular arc shape centered on the central axis of the syringe barrel body 40. The outer edge of each of the short axis direction side faces 44b viewed from the base end side has a linear shape which is parallel to the long axis direction. Each of the short axis direction side faces 44b may be a curved surface curved outward. The luer lock adapter 45 is a tube having a substantially hexagonal columnar outer shape and has an inner wall surface with a female thread (refer to FIG. 2A). The cap 24 with a male thread which seals the drug solution discharge portion 41 or a hub portion 22 of the injection hub 20 is detachably attached to the luer lock adapter 45 by thread engagement.

Figure 2A:
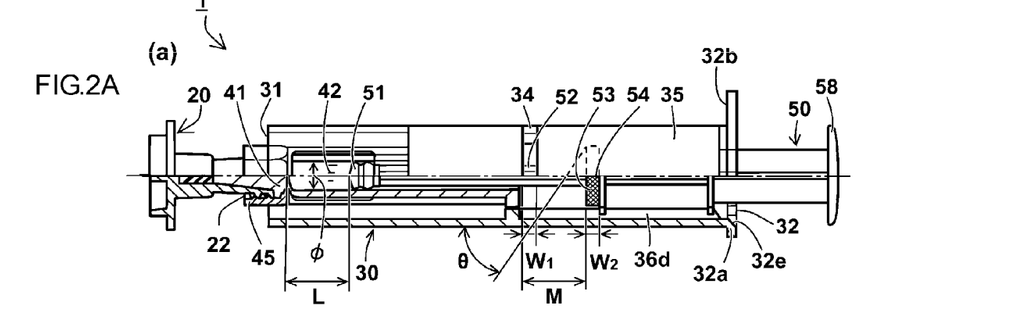
FIGS. 2A to 2C are partial sectional front views illustrating an embodiment of the prefilled syringe of the present invention when in use.

A drug solution 42 is stored in the inner space of the body 43 between the gasket 51 and the drug solution discharge portion 41 (refer to FIG. 2A). The cap 24 which seals the drug solution discharge portion 41 is detachably attached to the luer lock adapter 45 disposed on the tip of the syringe barrel body 40 by thread engagement. The gasket 51 slides toward the drug solution discharge portion 41. The slide of the gasket 51 allows the drug solution 42 to be discharged from the drug solution discharge portion 41. The inner diameter φ (refer to FIG. 2A) of the syringe barrel body 40 is preferably within the range of 4 to 7 mm.

The outer barrel body 30a is molded of a translucent resin. The outer barrel body 30a is substantially transparent enough to visually recognize the colors of a shaft 52 and a mark 54 located inside the outer barrel body 30a. The outer barrel body 30a has a substantially cylindrical shape having a barrel tip 31 and an opening 32. The outer barrel body 30a has an annular projection 32a located near the opening 32 and a flange-like finger catch 32b continuous with the annular projection 32a. The outer diameter and the inner diameter of the annular projection 32a are larger than those of the barrel tip 31. The finger catch 32b projects outward on the outer peripheral surface of the outer barrel body 30a. The finger catch 32b extends in a first direction in the radial direction which is substantially perpendicular to the central axis of the outer barrel 30 so as to project perpendicular to the central axis of the outer barrel 30. The finger catch 32b includes two parallel linear portions which are tangent lines of the annular projections 32a parallel to the first direction and a circular arc portions which connect the linear portions to each other, the circular arc portions being concentric with the barrel tip 31. The finger catch 32b projects only in the first direction in the radial direction which is perpendicular to the central axis of the outer barrel 30 on the outer peripheral surface of the annular projection 32a. Thus, use of the prefilled syringe 1 by gripping the outer barrel body 30a with an index finger 72, a middle finger 73, a ring finger 74, and a little finger 75 is obvious to an operator at a glance.

A substantially rectangular viewing hole 33 which penetrates a wall of the outer barrel body 30a is formed near the barrel tip 31 of the outer barrel body 30a. The viewing hole 33 is used by an operator for confirming the drug solution 42 before use. The viewing hole 33 exposes the gasket 51 which has reached the tip of the body 43 and the shaft 52 which abuts against the gasket 51 so as to be visually recognizable when discharge of the drug solution 42 is completed. Looking into the outer barrel body 30a through the viewing hole 33 enables a discharge state of the drug solution 42 and a sliding state of the gasket 51 inside the transparent syringe barrel body 40 to be clearly visually recognized without being obstructed.

Figure 3:
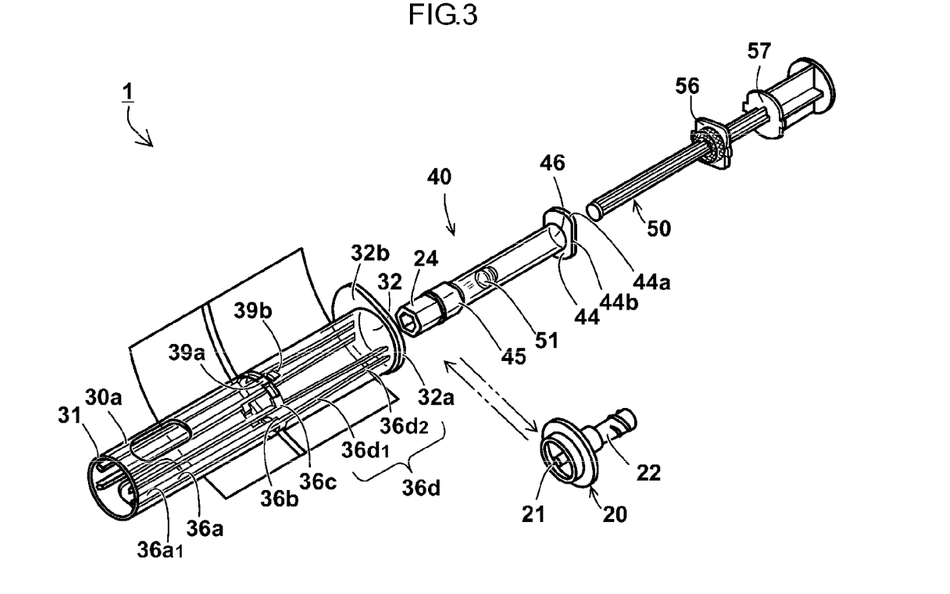
FIG. 3 is an exploded perspective view illustrating an embodiment of the prefilled syringe of the present invention.

As illustrated in FIG. 3, two pairs of linear guide ribs 36d are disposed on an inner wall surface of the outer barrel body 30a on the base end side thereof. Each of the two pairs of linear guide ribs 36d projects along the central axis of the outer barrel body 30a. The two pairs of linear guide ribs 36d are disposed at positions facing each other across the central axis of the outer barrel body 30a. Each of the two pairs of linear guide ribs 36d extends from the vicinity of the annular projection 32a up to the middle of the outer barrel body 30a. Each of the two pairs of linear guide ribs 36d includes a pair of base end side guide ribs 36d2 located between the middle and the base end thereof and a pair of tip side guide ribs 36d1 located between the middle and the barrel tip 31. The distance between the pair of tip side guide ribs 36d1 increases toward the barrel tip 31.

The distance between the guide ribs 36d that face each other is slightly larger than the width of a part of the syringe barrel flange 44, the part being inserted between the facing guide ribs 36d, and smaller than the width in the long axis direction of the syringe barrel flange 44. Accordingly, when the syringe barrel body 40 is inserted through the opening 32 of the outer barrel body 30a, the short axis direction side faces 44b of the syringe barrel flange 44 are guided by the guide ribs 36d, so that the syringe barrel body 40 is inserted into the outer barrel body 30a without rotating. The base end of each of the guide ribs 36d (base end side guide ribs 36d2) has a guide tapered portion 37b (refer to FIG. 2C) in which the height of the guide rib 36d decreases toward the opening 32.

As with the guide ribs 36d, two pairs of rotation restricting ribs 36c are disposed at positions facing each other across the central axis of the outer barrel body 30a. Each of the two pairs of rotation restricting ribs 36c projects from the inner wall surface of the outer barrel body 30a and faces the corresponding short axis direction side face 44b of the syringe barrel flange 44 of the syringe barrel body 40 inserted into the outer barrel body 30a on the tip of the corresponding pair of guide ribs 36d. Further, as with the rotation restricting ribs 36c, two pairs of support projections 36b are disposed at positions facing each other across the central axis of the outer barrel body 30a. Each of the two pairs of support projections 36b projects toward the central axis of the outer barrel body 30a at a position near the tip of the corresponding pair of rotation restricting ribs 36c. That is, each of the support projections 36b projects farther than the corresponding rotation restricting rib 36c to support a surface of the syringe barrel flange 44 of the syringe barrel body 40 inserted into the outer barrel body 30a, the surface facing the tip.

Further, four tilt restricting ribs 36a project from the inner wall surface of the outer barrel body 30a. The tilt restricting ribs 36a extend continuously from the respective support projections 36b up to the vicinity of the barrel tip 31. Two adjacent ones of the tilt restricting ribs 36a form a pair, and two pairs are disposed at positions facing each other across the central axis of the outer barrel body 30a. The tilt restricting ribs 36a are abuttable against the luer lock adapter 45 which is disposed on the tip of the syringe barrel body 40. Accordingly, when the syringe barrel body 40 is inserted into the outer barrel body 30a, tilt of the syringe barrel body 40 with respect to the outer barrel body 30a is restricted. The tip of each of the tilt restricting ribs 36a forms an abuttable portion 36a1 which is abuttable against the luer lock adapter 45 of the syringe barrel body 40 inserted into the outer barrel body 30a.

In the present embodiment, the guide rib 36d, the rotation restricting rib 36c, the support projection 36b, and the tilt restricting ribs 36a are continuously formed as one rib, and two pairs of ribs are disposed at positions facing each other across the central axis of the outer barrel body 30a as a whole. Alternatively, the guide rib 36d, the rotation restricting rib 36c, the support projection 36b, and the tilt restricting ribs 36a may be discontinuously formed.

Figure 5A:
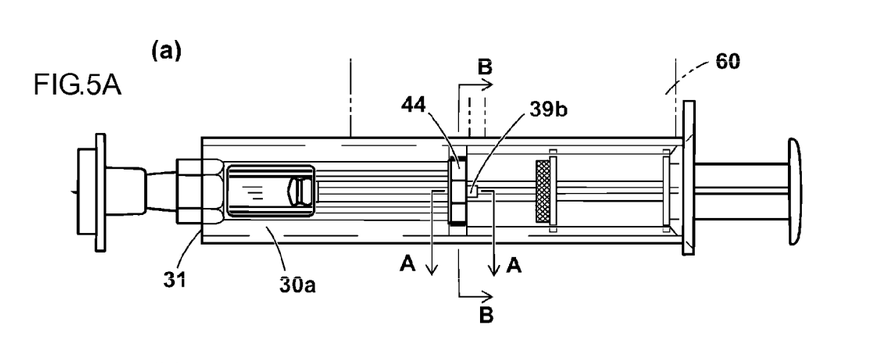
FIGS. 5A to 5C are, respectively, a side view, a sectional view, and a partially enlarged partial sectional view illustrating the embodiment of the prefilled syringe of the present invention.
Figures 5B, 5C:
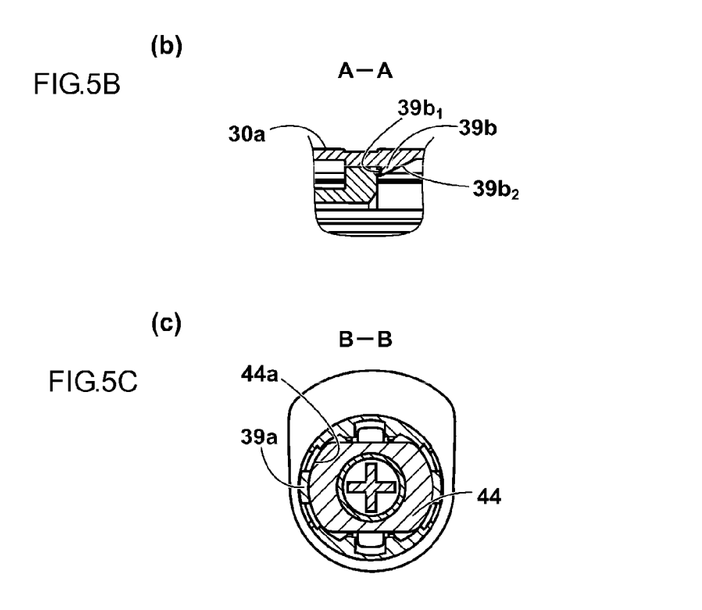
Figure 6A:
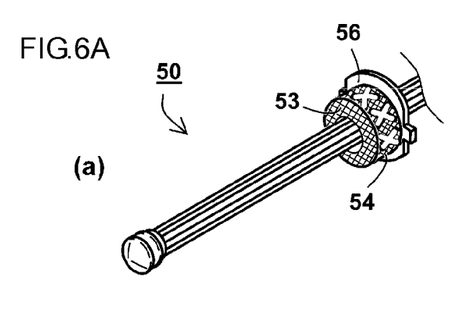
FIGS. 6A and 6B are partial perspective views illustrating another example of the plunger used in the prefilled syringe of an embodiment of the present invention.
Figure 6B:
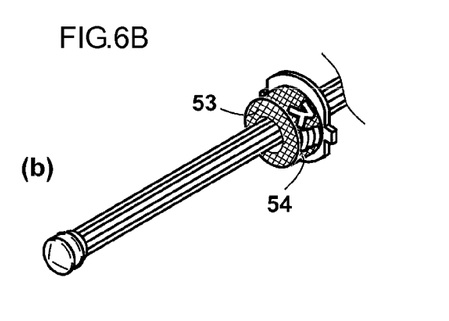

Further, two claws 39b are disposed at positions facing each other across the central axis of the outer barrel body 30a. Each of the claws 39b projects on the inner wall surface of the outer barrel body 30a at a position shifted by 90° in the circumferential direction of the outer barrel body 30a with respect to each of the two pairs of support projections 36b. Each of the claws 39b has a claw inclined surface 39b2 which is inclined so as to gradually reduce the distance from the central axis of the outer barrel body 30a toward the barrel tip 31 and a locking surface 39b1 which faces the barrel tip 31, the locking surface 39b1 being substantially perpendicular to the central axis of the outer barrel body 30a (refer to a partially enlarged view on arrows A of FIG. 5B).

By inserting the syringe barrel body 40 into the outer barrel body 30a, the syringe barrel flange 44 is held and locked between the locking surfaces 39b1 of the claws 39b and the support projections 36b. Further, each backlash restricting rib 39a abuts against the corresponding long axis direction side face 44a of the syringe barrel flange 44 to thereby restrict backlash in the long axis direction of the syringe barrel flange 44 with respect to the outer barrel body 30a (refer to a sectional view on arrows B of FIG. 5C). Further, the abuttable portions 36a1 abut against the side face of the luer lock adapter 45 to thereby restrict tilt of the syringe barrel body 40 with respect to the central axis of the outer barrel body 30a. In the prefilled syringe 1, backlash of the syringe barrel body 40 inside the outer barrel body 30a is restricted in this manner.

The plunger 50 has the shaft 52 whose cross section perpendicular to the axial direction thereof has a substantially cross shape. The tip side of the shaft 52 is inserted into the body 43 through the insertion port 46 of the syringe barrel body 40, and the tip of the shaft 52 abuts against the gasket 51. The shaft 52 has a press portion 58 located on the base end thereof for allowing the gasket 51 to slide by pressing to discharge the drug solution 42. The press portion 58 has a circular plate-like shape whose surface on the base end side is formed in a convex surface having a slightly swelling center.

A mark member 53 is fitted onto a part of the shaft 52 located between the insertion port 46 of the syringe barrel body 40 and the opening 32 of the outer barrel body 30a. The mark member 53 has a circular plate-like shape extending outward from the side face of the shaft 52. The outer diameter of the mark member 53 is larger than the inner diameter of the syringe barrel body 40 and smaller than the inner diameter of the outer barrel body 30a. A hole is formed on the center in the radial direction of the mark member 53. The inner diameter of the hole is slightly smaller than the outer diameter of the tip of the shaft 52 against which the gasket 51 abuts. The tip of the shaft 52 is pushed into the hole of the mark member 53 to thereby slightly expand the hole, so that the shaft 52 is fitted into the hole. Accordingly, the mark member 53 is attached to the shaft 52. The mark member 53 is formed of resin and therefore has slight flexibility. Thus, the mark member 53 generates stress in a direction for compressing the shaft 52. The mark member 53 is fixed to the shaft 52 by the stress.

The shaft 52 and the mark member 53 are molded of resins having different colors so that the difference in color between the shaft 52 and the mark member 53 is conspicuous. Thus, the entire outer peripheral surface of the mark member 53 functions as the mark 54 for allowing a medical worker to recognize a used condition of the prefilled syringe 1. Fitting the mark member 53 having a color different from the color of the shaft 52 onto the shaft 52 in this manner enables the mark 54 to be more easily formed than when the shaft 52 and the mark 54 are integrally molded by two-color molding.

The color of the mark member 53 is particularly preferably red. Red is generally a color indicating a warning. Thus, the red mark 54 is not overlooked, but immediately recognized by an operator, for example, a doctor. Examples of the red used in the mark 54 include vermilion, crimson, pink, orange, reddish pink, reddish orange, reddish brown, reddish yellow, and reddish violet. A specific chromaticity of the red preferably satisfies x=0.35 or more and y=0.45 or less regardless of the reflectance in an XYZ colorimetric system chromaticity diagram. The chromaticity of the red more preferably satisfies x=0.5 or more and y=0.35 or less because the red is more clearly conspicuous and thereby attracts the attention of a person who visually recognizes the mark 54. The color of the shaft 52 is preferably white or a complementary color of red, or a color approximate thereto. Accordingly, the difference in color between the shaft 52 and the mark 54 becomes further conspicuous.

When the amount of the drug solution 42 to be administered to a subject is small, specifically, 1 mL or less, the inner diameter φ (refer to FIG. 2A) of the syringe barrel body 40 is small, specifically, within the range of 4 to 7 mm. Using the outer peripheral surface of the mark member 53 which is thicker than the shaft 52 inserted into such a slim syringe barrel body 40 as the mark 54 enables the mark 54 to be conspicuous so as to be easily visually recognized.

A tip side flange 56 and a base end side flange 57 are formed on the shaft 52 in a manner to project from the side face of the shaft 52. The mark member 53 is positioned with respect to the shaft 52 by abutting against the tip side flange 56. The tip side flange 56 is larger than the mark member 53. Accordingly, when looking into the outer barrel body 30a through the opening 32, the mark member 53 cannot be visually recognized behind the tip side flange 56. The base end side flange 57 may be omitted.

The label 60 is a substantially rectangular film which has a first side 60a extending along the central axis thereof and a second side 60b extending along the circumferential direction thereof when cut and opened along the central axis of the outer barrel body 30a so as to be exploded. The length of the first side 60a is slightly shorter than the length between the tip of the finger catch 32b of the outer barrel body 30a and the base end of the viewing hole 33. The length of the second side 60b which is adjacent to the first side 60a is slightly longer than the circumferential length of the outer peripheral surface of the outer barrel body 30a.

The label 60 is a transparent film with opaque printing applied to substantially the entire surface thereof. The label 60 is provided with a band-like window forming transparent portion 63 having no printing which is formed between the middle and the tip of the label 60 and parallel to the second side 60b. The label 60 has a tip side opaque portion 62 located on the tip side and a base end side opaque portion 64 located on the base end side, the tip side opaque portion 62 and the base end side opaque portion 64 being divided by the window forming transparent portion 63. The color of the printing on the label 60 is different from the color of the mark 54, for example, white or a complementary color of red, or a color approximate thereto. Accordingly, the color of the label 60 makes the mark 54 conspicuous.

The label 60 is wrapped around the outer barrel body 30a to cover the outer peripheral surface of the outer barrel body 30a. Accordingly, the tip side opaque portion 62 and the base end side opaque portion 64 serve as the mask 35 which hides the inside of the outer barrel 30 on the outer peripheral surface of the wall of the outer barrel body 30a. The band-like window forming transparent portion 63 covers the entire circumference of the outer peripheral surface of the outer barrel body 30a located between the insertion port 46 of the syringe barrel body 40 and the opening 32 of the outer barrel body 30a. The window forming transparent portion 63 and the wall of the outer barrel body 30a together form the band-like window 34 which is substantially transparent enough to visually recognize the color of the mark 54 located inside the outer barrel 30. The window 34 preferably has a band-like shape extending over the entire circumference because the shaft 52 and the mark 54 located inside the outer barrel 30 can be visually observed from any direction.

The label 60 is wrapped around the outer barrel body 30a at a position between the finger catch 32b and the viewing hole 33 in such a manner that the label 60 does not cover the finger catch 32b and the viewing hole 33. This eliminates the necessity of forming a hole on the label 60 so as not to cover the viewing hole 33 or notching the label 60 corresponding to the finger catch 32b. The outer peripheral surface of the outer barrel 30 functions as a gripping portion gripped with at least the middle finger 73, the ring finger 74, and the little finger 75 when the drug solution 42 is administered. Thus, the window 34 is covered with the palm during the administration of the drug solution 42 (refer to FIG. 4).

As illustrated in FIG. 2A, a distance M between the tip side surface of the mark member 53 and the tip side edge of the window 34 is equal to a distance L between the tip of the gasket 51 and the base end of the drug solution discharge portion 41. Accordingly, the mask 35 hides the entire mark member 53 including the mark 54. In particular, an inclination A with respect to the central axis of the outer barrel 30 at which the mark member 53 is visually unrecognizable through the window 34 before use of the prefilled syringe 1 becomes 70° or more. That is, the mark member 53 cannot be visually recognized through the window 34 from a direction inclined by 70° or more with respect to the central axis of the outer barrel 30. Accordingly, misleading information of the prefilled syringe 1 having already been used is unlikely to be given to an operator before use of the prefilled syringe 1.

A width W1 of the window 34 along the central axis of the outer barrel 30 is preferably within the range of 0.5 to 1 mm. Accordingly, even when the movement distance of the plunger 50 between start and completion of discharge of the drug solution 42 is short, the mark member 53 cannot be visually recognized through the window 34 from a direction inclined by 70° or more with respect to the central axis of the outer barrel 30. Further, a width W2 of the mark member 53 along the central axis of the outer barrel 30 is also preferably within the range of 0.5 to 1 mm. This more surely makes the mark member 53 visually unrecognizable through the window 34 before use of the prefilled syringe 1.

Since the label 60 has the tip side opaque portion 62, the width of the red mark member 53 that can be visually recognized is limited to the width W1 of the window 34. Thus, even when looking into the outer barrel 30 through the window 34 with an inclination of less than θ before use of the prefilled syringe 1, the red mark member 53 is inconspicuous. Therefore, misleading information of the prefilled syringe 1 having already been used is unlikely to be given to an operator.

The outer diameter of the mark member 53 is preferably more than 0.65 times as large as the inner diameter of the outer barrel body 30a excepting the guide ribs 36d. Accordingly, even when the width W1 of the window 34 is narrow, specifically, within the range of 0.5 to 1 mm, the mark 54 can be sufficiently visually recognized through the window 34 after use of the prefilled syringe 1. This enables an operator to surely recognize that the prefilled syringe 1 has already been used.

The prefilled syringe mark member 53 operates in the following manner to allow use of the mark 54.

As illustrated in FIG. 2A, the mark member 53 remains stationary in a visually unrecognizable state, before the discharge of the drug solution 42, at a position where the mark 54 is covered with the mask 35. The prefilled syringe 1 in which the mark 54 is invisible indicates that the prefilled syringe 1 is unused.

Figure 2B:
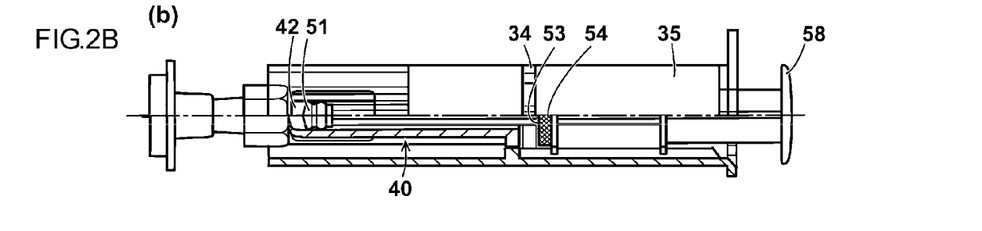

As illustrated in FIG. 2B, when the plunger 50 is pressed at the press portion 58, the gasket 51 starts sliding, and at the same time, the drug solution 42 is discharged from the syringe barrel body 40 and the mark member 53 starts moving toward the window 34.

Figure 2C:
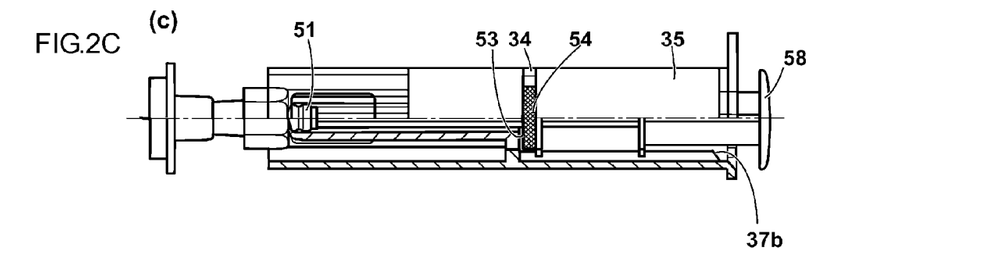

When the gasket 51 slides by the distance L, the discharge of the drug solution 42 is completed. Along with this, the mark member 53 moves by the distance M. As a result, as illustrated in FIG. 2C, the mark 54 comes to be visually recognizable through the window 34. The prefilled syringe 1 in which the mark 54 is visible indicates that the prefilled syringe 1 has already been used.

When the movement distance of the plunger 50 between start and completion of discharge of the drug solution 42 is short, and a part of the shaft 52 still projects from the opening 32 of the outer barrel 30 after the use of the prefilled syringe 1, it is difficult for the operator to distinguish between an unused condition and a used condition of the prefilled syringe 1 merely by a change in the length of the part of the shaft 52 projecting toward the base end side from the opening 32 of the outer barrel 30. Thus, when the movement distance of the plunger 50 is short, it is extremely useful that an unused condition and a used condition of the prefilled syringe 1 can be distinguished depending on whether the mark 54 is visually recognizable through the window 34. A thumb 71 which presses the press portion 58 of the plunger 50 may interfere with the finger catch 32b or the index finger 72 caught by the finger catch 32b or the middle finger 73 just before completion of the discharge of the drug solution 42, which may cause insufficient pressing to the plunger 50, and a prescribed amount of drug solution 42 may not be injected into the skin. Since a part of the shaft 52 still projects from the opening 32 of the outer barrel 30 after the use of the prefilled syringe 1, such a problem can be prevented. Further, it is also possible to prevent the thumb 71 which presses the press portion 58 from being caught between the opening 32 of the outer barrel 30 and the press portion 58 when discharge of the drug solution 42 is completed.

The mark 54 is covered with the mask 35 until just before completion of the discharge of the drug solution 42. Therefore, the operator may not misrecognize completion of the administration by visually observing the mark 54 during the discharge of the drug solution 42.

The prefilled syringe 1 is manufactured in the following manner.

The plunger 50 is manufactured in the following manner. The white shaft 52 which has the mark member 53, the flanges 56 and 57, and the press portion 58 is molded. The mark member 53 which has a hole for inserting the shaft 52 formed on the center thereof is molded of a resin which is colored in red with a coloring matter or pigment separately from the shaft 52. The shaft 52 is inserted into the hole of the molded mark member 53 from the tip of the shaft 52 to fit the mark member 53 onto the shaft 52. The tip of the shaft 52 is pushed into the hole of the mark member 53 to thereby slightly expand the hole, so that the shaft 52 is fitted into the hole. Accordingly, the mark member 53 is attached to the shaft 52. The mark member 53 is formed of resin and therefore has slight flexibility. Thus, the mark member 53 generates stress in a direction for compressing the shaft 52. The mark member 53 is fixed to the shaft 52 by the stress.

The syringe barrel body 40, the luer lock adapter 45, the cap 24, and the injection hub 20 are manufactured in the following manner. As illustrated in FIG. 3, the syringe barrel body 40, the luer lock adapter 45, and the cap 24 are separately injection molded. The luer lock adapter 45 is fitted onto the drug solution discharge portion 41 of the syringe barrel body 40. The cap 24 is attached to the luer lock adapter 45 by thread engagement. The hub portion 22 having an injection needle 21 which is arranged on the center of the hub portion 22 and penetrates the hub portion 22 is injection molded to form the injection hub 20.

Then, the outer barrel body 30a is manufactured in the following manner. The outer barrel body 30a which has the barrel tip 31, the viewing hole 33 which is open in a substantially rectangular shape, the opening 32, the annular projection 32a and the finger catch 32b both of which are located near the opening 32, the two pairs of guide ribs 36d, the two pairs of rotation restricting ribs 36c, the two pairs of support projections 36b, the two pairs of tilt restricting ribs 36a, the two backlash restricting ribs 39a, and the two claws 39b is injection molded.

Then, the drug solution 42 is filled in the following manner. First, the syringe barrel body 40 sealed by the cap 24 is subjected to autoclave sterilization or sterilization using ethylene oxide gas, γ rays, or electron beams. Then, a desired drug solution 42 is injected and filled into the body 43 of the syringe barrel body 40. Then, the gasket 51 is inserted into the syringe barrel body 40 to enclose the drug solution 42 therein.

Then, the prefilled syringe 1 is assembled in the following manner. The syringe barrel body 40 which stores the drug solution 42 therein is inserted into the outer barrel body 30a through the opening 32 of the outer barrel 30. The syringe barrel body 40 is pushed until the syringe barrel flange 44 climbs over the claws 39b to be locked between the support projections 36b and the claws 39b. Accordingly, the syringe barrel body 40 is locked to the outer barrel body 30a so as not to come off the outer barrel body 30a.

Then, the plunger 50 which has the mark member 53 is inserted into the outer barrel body 30a through the opening 32 of the outer barrel 30. The plunger 50 is pushed to allow the tip surface of the shaft 52 of the plunger 50 to come into contact with the base end surface of the gasket 51. In this manner, the prefilled syringe 1 with no label 60 wrapped is manufactured.

The label 60 is manufactured in the following manner separately from the manufacture of the prefilled syringe 1 with no label 60 wrapped. An opaque background color is printed on a long transparent film using ink of a color other than red with the window forming transparent portion 63 left. Further, for example, information regarding the drug solution 42 such as the kind, product name, active ingredient name, biological preparation indication, powerful drug indication, volume, names of manufacturer and distributor, lot number, and expiration date, or a figure is printed on the printed background color as needed. At last, the film is cut into a required length and wrapped around the prefilled syringe 1 with no label 60 wrapped to complete the manufacture of the prefilled syringe 1.

The obtained prefilled syringe 1 is air-tightly stored in a box-like blister packaging material having a film cover or a bag-like packaging material. The prefilled syringe 1 is sterilized together with the packaging material. The injection hub 20 is covered with a cap (not illustrated) to protect the injection needle 21 as needed and stored in a sterilized and sealed cup-like blister packaging material.

In the prefilled syringe 1, the coloring matter or pigment of the mark 54 does not make direct contact with the drug solution 42. Thus, the coloring matter or pigment is not eluted into the drug solution 42. Therefore, the safety can be ensured.

The prefilled syringe 1 is not limited to the embodiment illustrated in FIGS. 1 to 3 as long as it has the mask 35 which covers the mark 54 so as to be visually unrecognizable and the window 34 which exposes the mark 54 so as to be visually recognizable when the discharge of the drug solution is completed.

The shaft 52, the mark member 53, the mark 54, the flanges 56 and 57, and the press portion 58 may be colored by application of ink, printing, single-color molding, or two-color molding. For example, a mark member 53 may be molded of a white resin and a mark 54 may be printed on the mark member 53 using a red paint or pigment. Alternatively, a mark member 53 in which only the outer periphery thereof is red may be molded or a white shaft 52 and a red mark member 53 may be integrally molded by two-color molding.

The colors of characters, figures, and background on the mask 35 are preferably different from the color of the mark 54.

The window 34 may be formed from the substantially transparent outer barrel body 30a and an exposure portion 38 which is interposed between a pair of labels 60 which separately forms only the base end side opaque portion 64 and the tip side opaque portion 62 in a manner to surround the outer barrel body 30a. That is, the exposure portion 38 may be formed on the pair of labels 60.

The window 34 may be intermittently formed around the central axis of the outer barrel body 30a. Holes may be intermittently formed on a part of the opaque label 60 along the circumferential direction thereof, and the holes and the substantially transparent outer barrel body 30a may together form the window 34. The outer barrel body 30a may be molded of an opaque resin and holes may be intermittently formed on a part of the outer barrel body 30a along the circumferential direction thereof to form the window 34. In this case, the label 60 is stuck at a position that does not cover the window 34.

A taper 32e (refer to FIG. 2A) whose distance from the central axis of the outer barrel body 30a gradually decreases toward the barrel tip 31 may be formed on the inner wall surface of the annular projection 32a. The flanges 56 and 57 are slidingly guided to the guide ribs 36d by the taper 32e when the plunger 50 is inserted into the outer barrel 30. Thus, the plunger 50 can be smoothly inserted into the outer barrel 30. As illustrated in FIG. 2A, tapers 32e may be formed along the inner wall surface of the annular projection 32a at certain intervals or a taper 32e may be formed throughout the entire circumference.

Next, a method of using the prefilled syringe 1 will be described.

A backing paper of the blister packaging material is peeled off to take out the prefilled syringe 1. Then, the cap 24 attached to the luer lock adapter 45 is detached. Then, the film cover of the blister packaging material which stores the injection hub 20 is peeled off. Then, the injection hub 20 is screwed with the luer lock adapter 45 so as to be attached to the drug solution discharge portion 41 instead of the cap 24. The prepared and unused prefilled syringe 1 is placed on a preparation table. Even if unused and used prefilled syringes 1 are mistakenly mixed, it is possible to surely distinguish and eliminate a used prefilled syringe 1 so as not to be used by confirming whether the mark 54 is substantially visually recognizable or unrecognizable.

Figure 4:
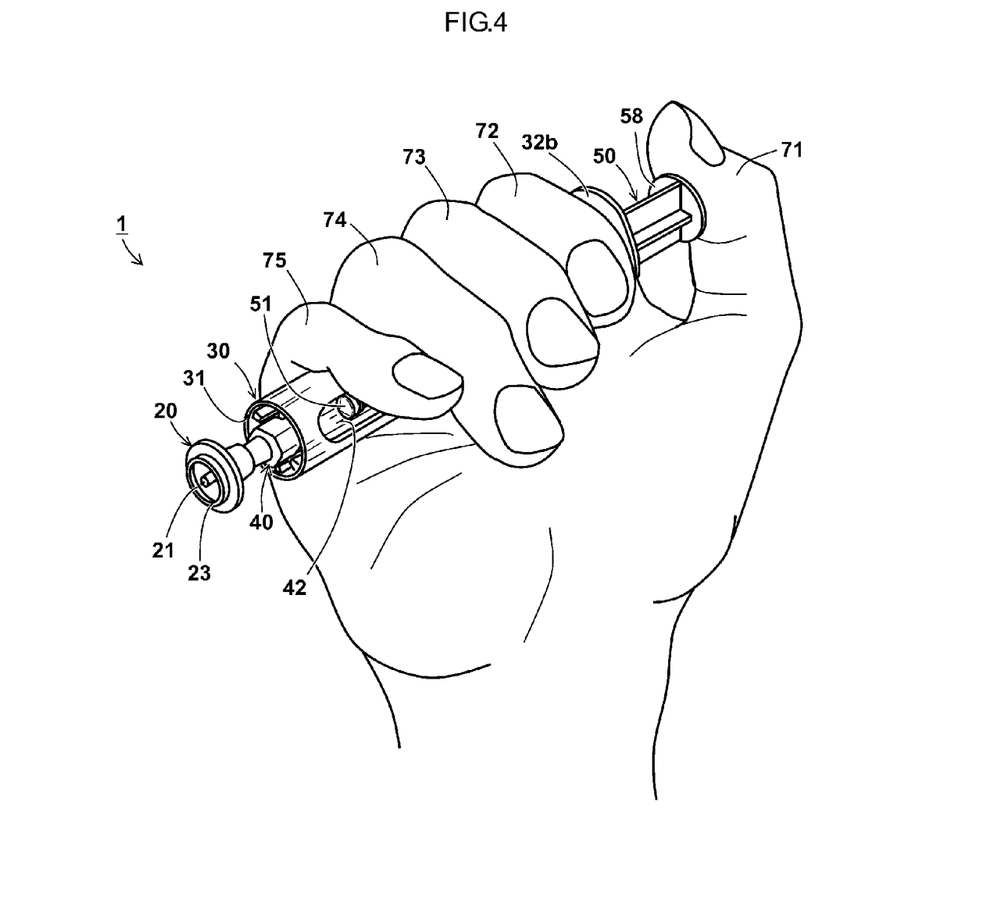
FIG. 4 is a perspective view illustrating an embodiment of the prefilled syringe of the present invention when in use.

An unused prefilled syringe 1 that has been confirmed as having the mark 54 that cannot be substantially visually observed through the window 34 is used for injection. For example, a doctor takes the prefilled syringe 1, detaches the cap (not illustrated) of the injection hub 20, and, as illustrated in FIG. 4, grips the outer barrel 30 with the entire palm while allowing the index finger 72 to abut against the tip side surface of the finger catch 32b. An annular stabilizing portion 23 of the injection hub 20 is pressed against the skin of a subject while putting the thumb 71 onto the press portion 58 of the plunger 50 and the injection needle 21 is surely inserted into the skin. Then, the plunger 50 is pressed to allow the gasket 51 to slide toward the tip side to thereby administer the drug solution 42 to the subject from the syringe barrel body 40 through the injection needle 21. Even if the pressing force to the press portion 58 is high, the finger catch 32b catching the index finger 72 prevents the fingers gripping the outer barrel 30 from being further displaced toward the base end side with respect to the outer barrel 30. Thus, the drug solution 42 can be stably administered. Further, when the drug solution 42 is being administered, the window 34 is covered with the palm. Thus, the operator can concentrate on the administration without being disturbed by the appearance of the conspicuous mark 54.

After completion of the administration of the drug solution 42, the prefilled syringe 1 is removed from the subject together with the injection needle 21.

The window 34 is located at a conspicuous position between the middle and the base end of the outer barrel 30. Thus, when looking or taking the prefilled syringe 1, the window 34 surely comes into sight. Therefore, it is possible to have a glance at the mark 54 through the window 34. As a result, it is possible to more surely recognize that the prefilled syringe 1 has already been used.

Although the preferred embodiment of the prefilled syringe 1 has been described with reference to FIGS. 1 to 5C, other embodiments as illustrated in FIGS. 6A to 9 may be employed.

An outlined symbol indicating a used condition, for example, "x" (FIG. 6A) or an outlined character indicating a used condition, for example, "USED" (FIG. 6B) may be put on the mark 54 of the mark member 53. Alternatively, any pattern or figure indicating a used condition may be put on the mark 54.

The mask 35 may be an opaque coating formed by coating the outer barrel body 30a with paint.

The label 60 may be stuck to the outer barrel body 30a to cover the outer barrel body 30a. Alternatively, the label 60 may be previously formed into a tube that is larger than the outer barrel body 30a and allowed to shrink to cover the outer barrel body 30a.

Figure 7:
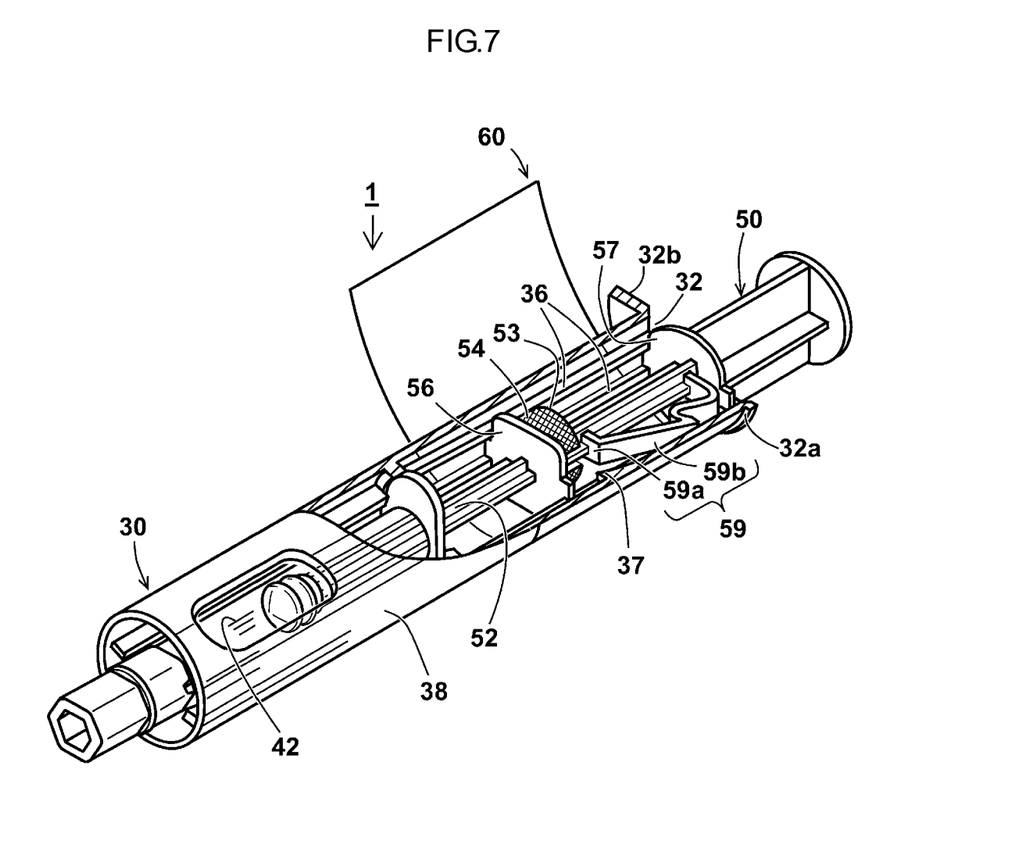
FIG. 7 is a partially cut-away perspective view illustrating another embodiment of the prefilled syringe of the present invention.

FIG. 7 is a partially cut-away perspective view illustrating another embodiment of the prefilled syringe 1. In the prefilled syringe 1 of this embodiment, a label 60 which includes only a base end side opaque portion 64 covers an outer barrel body 30a. A part of the outer barrel body 30a that is not covered with the label 60 forms an exposure portion 38. A mark member 53 which is molded separately from a plunger 50 is attached to a shaft 52 on the base end side with respect to a tip side flange 56. A vibrator 59 for generating a click sound and click vibration during the discharge of the drug solution 42 is disposed on the base end side with respect to the mark member 53.

The mark member 53 has a hole into which the shaft 52 is fitted and a cut-away part which extends from the outer peripheral surface to the hole. The cut-away part of the mark member 53 is opened and the shaft 52 is inserted into the hole of the mark member 53, so that the mark member 53 is attached to the shaft 52 inside an outer barrel 30 on the base end side with respect to the tip side flange 56. A mark 54 of the mark member 53 is obstructed by the tip side flange 56 and hardly in sight through the window 34 when the prefilled syringe 1 is unused. Although the mark 54 is disposed on the base end side with respect to the tip side flange 56, the mark 54 is hardly in sight when looking into the outer barrel 30 through an opening 32 because of the existence of a base end side flange 57 which is located near the base end side of the opening 32.

The vibrator 59 branches and projects from the side face of the shaft 52 on the base end side with respect to the mark member 53. The vibrator 59 is a thin plate which includes a flexible portion 59a and a sliding portion 59b. The flexible portion 59a projects outward with respect to the central axis of the shaft 52. The sliding portion 59b is continuous with the flexible portion 59a and has an inclined portion which slides on a bump 37 of the outer barrel 30. The bump 37 projects on the base end side in a manner to prevent contact with a projection of the tip side flange 56 between a pair of guide ribs 36d. The bump 37 is formed at a position where the further projecting top of the vibrator 59 climbs over the bump 37 just when the discharge of the drug solution 42 is completed.

Figure 8A:
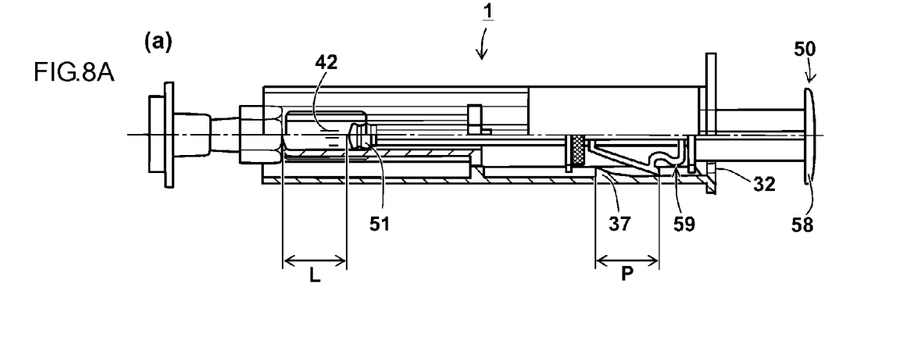
FIGS. 8A to 8C are partial sectional front views illustrating another embodiment of the prefilled syringe of the present invention when in use.
Figure 8B:
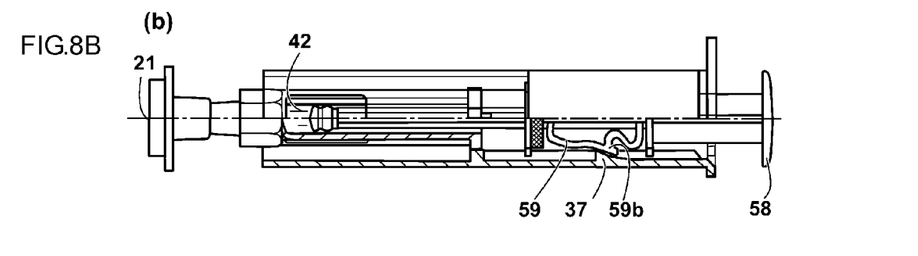
Figure 8C:
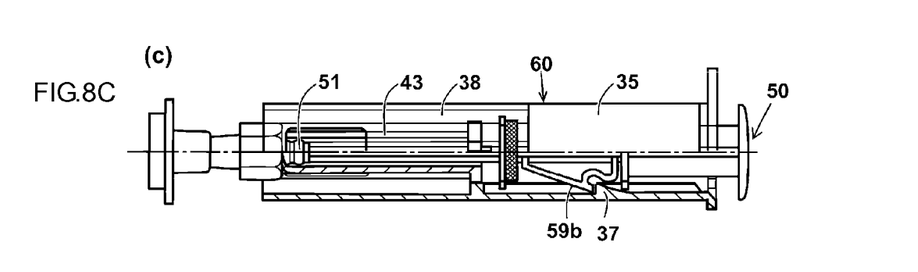

FIGS. 8A to 8C are partial sectional views illustrating a state of the prefilled syringe 1 when in use. FIG. 8A illustrates a state of the prefilled syringe 1 just before being used in which a press portion 58 projects from the opening 32. A sliding distance L by which the gasket 51 slides until completion of the discharge of the drug solution 42 is substantially equal to a movement distance P by which the plunger 50 moves until the vibrator 59 climbs over the bump 37. Accordingly, the vibrator 59 climbs over the bump 37 almost simultaneously with the completion of the discharge of the drug solution 42 by the gasket 51 reaching the tip of the body 43.

FIG. 8B illustrates the prefilled syringe 1 when the drug solution 42 is being discharged. FIG. 8B illustrates a state in which the drug solution 42 is being discharged from the injection needle 21 by pressing the press portion 58. The vibrator 59 climbs on the bump 37 by the sliding portion 59b sliding on an inclined surface of the bump 37. The inclined surface of the bump 37 is slightly curved in such a manner that the slope thereof becomes steeper toward the tip. Thus, the stress is rapidly increased as the sliding portion 59b comes close to the tip of the bump 37 by pressing the press portion 58. The sliding portion 59b is biased toward the inclined surface of the bump 37 by the stress. Thus, frictional resistance is generated between the sliding portion 59b and the inclined surface of the bump 37.

FIG. 8C illustrates the prefilled syringe 1 when the discharge of the drug solution 42 is completed. FIG. 8C illustrates a state in which the plunger 50 is completely pressed and the gasket 51 reaches the tip of the body 43. The sliding portion 59b climbs over the top of the bump 37 almost simultaneously with the reaching of the gasket 51, and the stress accumulated on the vibrator 59 is immediately released from the acute top of the bump 37. This flips the vibrator 59 to vibrate to simultaneously generate a click sound and click vibration. For example, a doctor can recognize that the discharge of the drug solution 42 has been completed or almost completed by catching the click sound or sensing the click vibration. Further, a click sound and click vibration give a human a feeling of completion of a desired operation. Thus, the prefilled syringe 1 can give, for example, a doctor a sense of security such that the drug solution 42 has been surely administered to a subject.

Further, the appearance of the mark 54 which has been covered with the mask 35 on the exposure portion 38 can be visually observed together with a discharge state of the entire drug solution 42 and an operation state of the gasket 51 and the shaft 52 when the discharge of the drug solution 42 is completed.

Figure 9:
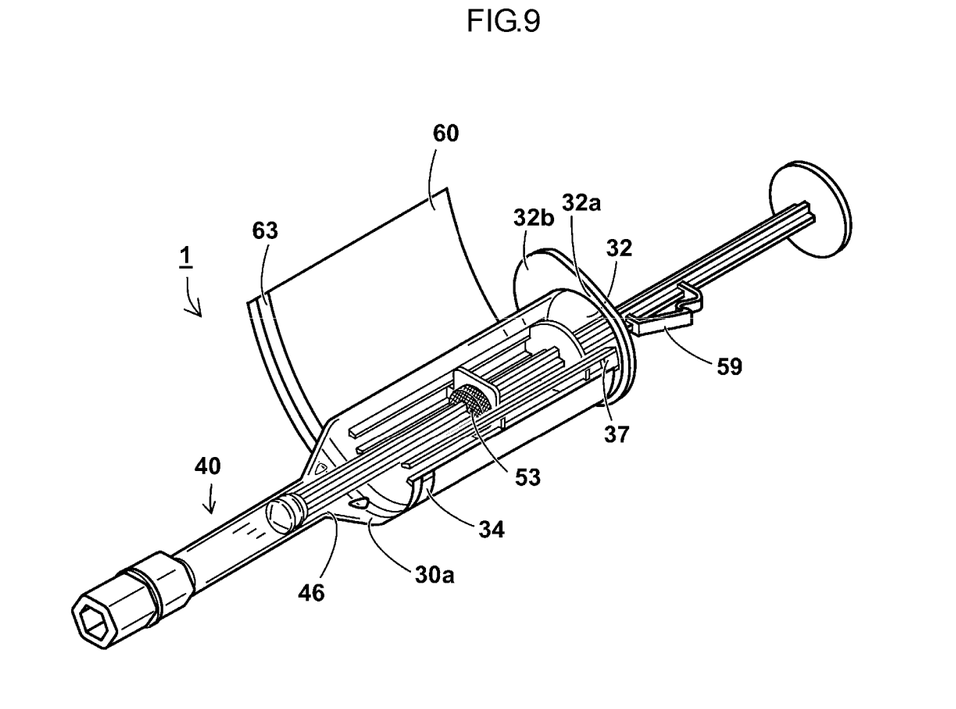
FIG. 9 is a partially exploded perspective view illustrating another embodiment of the prefilled syringe of the present invention.

FIG. 9 is a partially exploded perspective view illustrating another embodiment of the prefilled syringe 1. In the prefilled syringe 1 illustrated in FIG. 9, an outer barrel body 30a and a syringe barrel body 40 are integrated. The outer barrel body 30a extends from the circumference of an insertion port 46 of the syringe barrel body 40 toward an opening 32. The outer barrel body 30a has an inner diameter larger than the inner diameter of the syringe barrel body 40 and a bump 37 which is formed on the base end side with respect to the insertion port 46. The outer barrel body 30a further has an expanded diameter portion which expands from the circumference of the insertion port 46 toward the opening 32. The outer barrel body 30a is connected to the syringe barrel body 40 through the expanded diameter portion. Through holes which form steps are symmetrically formed with respect to the central axis of the expanded diameter portion. In the prefilled syringe 1, a mark member 53 is exposed through a window 34 almost simultaneously with completion of the discharge of a drug solution 42, and a vibrator 59 is flipped to generate a click sound and click vibration.

Examples of the drug solution 42 stored in the syringe barrel body 40 include bio-pharmaceuticals such as vaccines for preventing influenza, tetanus, Streptococcus pneumoniae, poliomyelitis, Japanese encephalitis, rubella, measles, yellow fever, Hib, hepatitis, chicken pox, rabies, rotavirus, mumps, and cervical cancer, and MQ, DT, and DPT vaccines. Examples of the drug solution 42 other than vaccines include a carbohydrate injection such as glucose, an injection for electrolyte correction such as sodium chloride and potassium lactate, a contrast agent, a steroid, a protease inhibitor, fat emulsion, an antibiotic, an anticancer agent, heparin calcium, an anesthetic, and an antibody preparation.

When a small amount of drug solution 42 is administered using the prefilled syringe 1, the movement distance of the plunger 50 during the administration is short. When a part of the shaft 52 still projects from the opening 32 of the outer barrel 30 after the use of the prefilled syringe 1, it is difficult for an operator to distinguish between an unused condition and a used condition of the prefilled syringe 1 merely by a change in the length of the part of the shaft 52 projecting toward the base end side from the opening 32 of the outer barrel 30. Thus, the prefilled syringe 1 is preferably used when the movement distance of the plunger 50 is short. In particular, when the drug solution 42 is administered into the skin, the movement distance of the plunger 50 between start and completion of discharge of the drug solution 42 is extremely short, specifically, within the range of 5 to 16 mm. Therefore, the prefilled syringe 1 is particularly preferably used in such a case.

The materials of the outer barrel body 30a, the syringe barrel body 40, the luer lock adapter 45, the cap 24, the shaft 52, the mark member 53, the flanges 56 and 57, the press portion 58, and the body of the injection hub 20 are selected in view of, for example, the chemical resistance, gas/bacteria barrier properties, and the safety to a living body. For example, polyolefin resins such as polyethylene, polypropylene and cyclic polyolefin, polystyrene, polycarbonate, polyester such as polyethylene-terephthalate, and polyamide are used. In particular, when autoclave sterilization is performed, a resin having a high heat resistance, for example, polypropylene or polycarbonate is preferably used as the materials of these members. Further, a cyclic olefin homopolymer or a cyclic olefin copolymer which is a resin having a high transparency so as to visually recognize the drug solution 42 stored in the barrel from the outside, having a less interaction with the drug solution 42, and having a stiffness enough to prevent the outer barrel body 30a and the syringe barrel body 40 from being bent and crushed even by being strongly gripped or pushed during administration of the drug solution 42 is preferably used as the materials of the outer barrel body 30a and the syringe barrel body 40. These members are formed by molding. Examples of the molding include injection molding, blow molding, and thermoforming. Among these molding methods, injection molding is preferably used.

The material of the gasket 51 is selected from a point of view similar to the above. For example, olefin-based, polyurethane-based, polyester-based, polyamide-based and styrene-based thermoplastic elastomers, and rubber materials such as natural rubber, isoprene rubber, butadiene rubber, styrene-butadiene rubber, and silicone rubber are used.

The embodiments illustrated in FIGS. 1 to 5C, 6A and 6B, 7 to 8C, and 9 can be appropriately combined. For example, the vibrator 59 and the bump 37 described in the embodiment illustrated in FIGS. 7 to 8C may be combined with the embodiment illustrated in FIGS. 1 to 5C.

The prefilled syringe of the present invention is used for administering a small amount of drug solution to a subject.

What is claimed is:

1. A prefilled syringe comprising:
   a syringe barrel including a syringe barrel body and an outer barrel, the syringe barrel body having a drug solution discharge portion located on a tip end and an insertion port open on a base end, at least a part of the outer barrel extending in a tubular shape from the insertion port toward a base end side, the outer barrel having an opening located on a base end and having an inner diameter that is larger than an inner diameter of the syringe barrel body in a region between the insertion port and the opening;
   a cap configured to seal the drug solution discharge portion;
   a gasket disposed in the syringe barrel body;
   a plunger having a shaft disposed in the syringe barrel through the opening and a press portion disposed on a base end of the shaft, the plunger being configured to move toward the tip end by a pressing operation to the press portion to allow the gasket to slide toward the drug solution discharge portion; and
   a drug solution stored between the drug solution discharge portion and the gasket inside the syringe barrel body, the drug solution being dischargeable from the drug solution discharge portion by the sliding of the gasket,
   wherein the outer barrel includes a window formed on a wall of the outer barrel located between the insertion port and the opening of the outer barrel, and a mask configured to hide an inside of the outer barrel,
   wherein a mark is disposed on a part of the shaft located between the insertion port and the opening of the outer barrel, the mark having an outer diameter larger than the inner diameter of the syringe barrel body at the base end of the syringe barrel body, at least an outer peripheral surface of the mark having a color that is different from a color of other parts of the plunger,
   wherein, before discharge of the drug solution, the outer peripheral surface of the mark is covered with the mask such that the mark is not visually recognizable through the window from a direction inclined by 70° or more with respect to a central axis of the outer barrel, and wherein, after discharge of the drug solution is completed, the outer peripheral surface of the mark, which has moved along with movement of the plunger toward the tip end, is visually recognizable through the window.

2. The prefilled syringe according to claim 1, wherein the mark comprises a mark member that is fit onto said part of the shaft, at least an outer peripheral surface of the mark member having the color that is different from the color of the other parts of the plunger.

3. The prefilled syringe according to claim 2, wherein:
the outer barrel includes a substantially transparent outer barrel body and a label, the label circumferentially covering an outer peripheral surface of the outer barrel body, and the label including a transparent portion or an exposure portion at which a part of the outer peripheral surface of the outer barrel body is exposed, and two opaque portions located on a tip end side and a base end side of the transparent portion,
the window comprises a part of a wall of the outer barrel body and the transparent portion or the exposure portion of the label, and
the mask comprises the opaque portions.

4. The prefilled syringe according to claim 3, wherein the window is circumferentially continuous around a central axis of the outer barrel body.

5. The prefilled syringe according to claim 3, wherein the window is circumferentially intermittent around a central axis of the outer barrel body.

6. The prefilled syringe according to claim 3, wherein a width of the transparent portion or the exposure portion in a central axis direction of the outer barrel is in a range of 0.5 to 1 mm.

7. The prefilled syringe according to claim 4, wherein a width of the transparent portion or the exposure portion in a central axis direction of the outer barrel is in a range of 0.5 to 1 mm.

8. The prefilled syringe according to claim 5, wherein a width of the transparent portion or the exposure portion in a central axis direction of the outer barrel is in a range of 0.5 to 1 mm.

9. The prefilled syringe according to claim 2, wherein the mark member has a ring-like shape, a part of which has a cut-away part, and is fittable onto the shaft from a direction substantially perpendicular to a central axis of the shaft using the cut-away part.

10. The prefilled syringe according to claim 9, wherein the shaft has a tip side flange located on the tip side with respect to the mark member, the tip side flange extending in a direction substantially perpendicular to the central axis of the shaft.

11. The prefilled syringe according to claim 10, wherein, before discharge of the drug solution, the tip side flange is located on the base end side with respect to the window.

12. The prefilled syringe according to claim 11, wherein the shaft has a base end side flange located between the mark and the opening, the base end side flange extending in a direction substantially perpendicular to the central axis of the shaft.

13. The prefilled syringe according to claim 2, wherein:
the outer barrel includes a substantially transparent outer barrel body and a label, the label circumferentially covering an outer peripheral surface of the outer barrel body and having an opaque portion serving as the mask, and
the window includes a wall of the outer barrel body that is not covered by the label.

14. The prefilled syringe according to claim 1, wherein a maximum movement distance of the plunger between start and completion of discharge of the drug solution is 15 mm.

15. The prefilled syringe according to claim 1, wherein the inner diameter of the syringe barrel body is 7 mm or less.

* * * * *